United States Patent [19]

Schwartz

[11] 4,413,987
[45] Nov. 8, 1983

[54] WOUND IRRIGATION SYSTEM
[76] Inventor: Nathan H. Schwartz, P.O. Box 1643, Smyrna, Ga. 30081
[21] Appl. No.: 345,003
[22] Filed: Feb. 2, 1982
[51] Int. Cl.³ ............................................. A61M 1/00
[52] U.S. Cl. ........................................ 604/28; 604/35
[58] Field of Search ...................... 604/27, 28, 35, 51, 604/289, 290, 313, 315, 118, 119

[56] References Cited
U.S. PATENT DOCUMENTS

| | | | |
|---|---|---|---|
| 946,256 | 1/1910 | McNerthney | 604/35 |
| 1,114,268 | 10/1914 | Kells | 604/27 |
| 1,758,332 | 5/1930 | Pittman et al. | 604/35 |
| 2,568,566 | 9/1951 | Sokolik | 604/35 |
| 3,993,080 | 11/1976 | Loseff | 604/28 |
| 4,098,275 | 7/1978 | Consalvo | 604/27 |

Primary Examiner—John D. Yasko
Attorney, Agent, or Firm—B. J. Powell

[57] ABSTRACT

A method of irrigating a wound in a body part with a treatment liquid including the steps of placing a piece of tubing having a perforated section therein in the body part so that the perforated section is located in the vicinity of the wound in the body part to be irrigated; connecting one end of the tubing to a source of the treatment liquid so that the treatment liquid passes through the tubing into the body part and is discharged into the wound through the perforated section; and connecting the opposite end of the piece of tubing to a vacuum source so that a vacuum can be imposed through the tubing on the treatment liquid passing into the body part through the tubing and through the perforated section on any liquid in the body part to withdraw same. The apparatus for carrying out the method is also disclosed.

6 Claims, 5 Drawing Figures

WOUND IRRIGATION SYSTEM

BACKGROUND OF THE INVENTION

This invention relates generally to irrigation apparatus and more particularly to irrigation apparatus for use in irrigating portions of body parts with a treatment solution to prevent or reduce infection.

Irrigation of a portion of a body part with a treatment solution quite often becomes necessary to prevent or reduce infection. Where the body has a natural cavity therein, such as a bladder or other similar organ, catheterization has been used to introduce the treatment solution into the organ and to drain fluid from the organ by gravity. Where the body part has no such natural cavity as is the case with bones, muscles and the like or a foot, arm, hand or the like, the treatment solution is typically introduced into the body part through a perforated section in a piece of tubing. Another piece of tubing connected to a vacuum source is positioned in the body part at a position spaced from the injection tubing so that the treatment solution must migrate through the body part from the injection tubing to the vacuum tubing before being withdrawn. Both of these prior art irrigation techniques have problems associated with the use thereof. One of the primary problems associated therewith is that the drain from the body part frequently becomes blocked, thereby requiring frequent monitoring to see if the drain is blocked. Further appropriate cleaning techniques must be used to clear this blockage. Another problem associated therewith is that surgical procedures are frequently required to install and/or remove the irrigation apparatus from the body part.

SUMMARY OF THE INVENTION

These and other problems associated with the prior art are overcome by the invention disclosed herein by providing an irrigation apparatus and technique which is not subject to drain blockage and which can be installed without resort to surgical procedures.

The irrigation apparatus of the inventon includes a piece of tubing that is passed through the body part. The tubing has a fluid passage therethrough and is provided with a perforated section corresponding in length to that portion of the body part to be irrigated. The perforated section is located in registration with that portion of the body part to be irrigated. One end of the tubing is connected to a fluid source for supplying the treatment solution to the fluid passage in the tubing at a controlled rate while the other end of the tubing is connected to a vacuum source.

The fluid source continuously supplies treatment solution to the fluid passage in the tubing while the vacuum may be intermittently imposed in the fluid passage in the tubing. Thus, while the vacuum is not being imposed, the treatment solution flows along the fluid passage and is forced out through the perforated section of the tubing into the body part. When the vacuum source is operating, a vacuum is imposed through the perforated section of the tubing to withdraw the fluid in the body part around the perforated section of the tubing out of the other end of the tubing. At the same time, however, the vacuum is also imposed on the treatment fluid between the fluid source and the perforated section in the tubing so that some of this treatment fluid is also withdrawn through the other end of the tubing along with the fluid from the body part to keep the fluid passage in the tubing flushed out. Since fluid is alternately discharged out through the perforated section and then sucked in through the perforated section, this action keeps the perforations open to prevent blockage of the perforations.

Since the tubing passes through the body part, installation is simplified. A solid needle is fitted in one end of the piece of tubing and passed through the body part pulling the tubing therebehind. After the tubing is in place, the needle is removed and the connections made to carry out the irrigation procedure.

A venting means is provided between the fluid source and body part to permit air to be drawn through the tubing in the body part when a vacuum is being imposed. This permits a sufficient volume to be withdrawn to insure that the fluid from the body part will be withdrawn when the vacuum is imposed.

These and other features and advantages of the invention disclosed herein will become more apparent upon consideration of the following specification and accompanying drawings wherein like characters of reference designate corresponding parts throughout the several views and in which:

Figure 1:
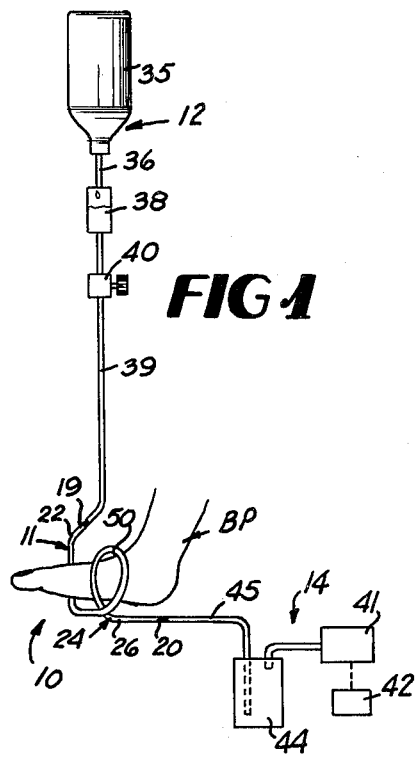
FIG. 1 is a view illustrating the invention.

These figures and the following detailed description disclose specific embodiments of the invention; however, it is to be understood that the inventive concept is not limited thereto since it can be incorporated in other forms.

DETAILED DESCRIPTION OF ILLUSTRATIVE EMBODIMENTS

Referring to the drawings, the irrigation system 10 includes an elongate irrigation tube 11 adapted to be passed through the body part BP to be irrigated, a fluid source 12 connected to one end of the irrigation tube 11, and a vacuum source 14 connected to the opposite end of the tube 11. The treatment solution is supplied from the fluid source 12 to the body part via tube 11 and fluids are withdrawn from the body part by the vacuum source 14 via the tube 11. While the system 10 is illustrated being applied to a foot, it is to be understood that the system 10 may be easily used to irrigate any body part or portion thereof such as a hand, leg, arm, finger, toe or the like.

The irrigation tube 11 has a seamless tubular side wall 15 defining a fluid passage 16 therethrough along the length of tube 11. Side wall 15 is typically made out of a flexible plastic material. Side wall 15 has a perforated section 18 therein intermediate its ends with a prescribed length $L_P$ corresponding to the length of that portion of the body part BP to be irrigated. The tube 11 is installed in the body part BP so that the perforated section 18 is in registration with that portion to be irrigated and with opposite ends 19 and 20 of the tube 11 projecting out of the body part. That end 19 of tube 11 is adapted to be connected to the fluid source 12 while that end 20 of tube 11 is adapted to be connected to vacuum source 14.

The perforated section 18 of side wall 15 defines a plurality of discharge openings 21 therethrough axially spaced along section 18 and circumferentially spaced about section 18. These openings 21 communicate with the fluid passage 16 so that fluid can flow from passage 16 out through openings 21 or into passage 16 through openings 21 as will become more apparent. The diameter of openings 21 is smaller than the diameter of fluid passage 16 to help prevent blockage of passage 16 as will become more apparent.

For purposes of identification, that section of tube 11 between the perforated section 18 and end 19 will be called the inlet section 22 while that section of the tube 11 between the perforated section 18 and end 20 will be called the discharge section 24. Typically, the inlet section 22 has the same diameter as the perforated section 18 and this section is passed through the body part to locate the perforated section 18 in registration with that portion of the body part BP to be irrigated as will become more apparent. The discharge section 24 may likewise have the same diameter as the perforated section 18, although, in the preferred arrangement illustrated, the discharge section 24 has an inboard portion 25 of the same diameter as the perforated section 18 with a length $L_I$ such that the portion 25 extends from the perforated section 18 to the exterior of the body part BP. Section 24 also has an outboard portion 26 connected to the inboard portion 25 by a tapered transition portion 28. The outboard portion 26 has a larger diameter than the perforated section 18 with the transition portion 28 tapering inwardly from the diameter of portion 26 down to the diameter of inboard portion 25. The transition portion 28 also serves to provide a seal around the tube 11 at the surface of the body part BP as will become more apparent. An attachment tab 29 may be provided on the discharge section 24 at the transition portion 28 for attaching the tube 11 to the body part BP such as by suturing to hold the tube 11 in place during use.

It will be appreciated that the tube 11 will be made in different sizes so that the diameter of the fluid passage 16 through the perforated section 18 will be of different sizes. This is necessary to provide for the different flow rates of the treatment fluid to be used to irrigate the body part BP and to insure that the perforated section 18 is small enough to be placed in different body parts BP. It will also be appreciated that the tube 11 will be made with perforated sections 18 of different lengths $L_P$ so that a tube 11 can be selected with a perforated section 18 therein that matches the length of that portion of the body part BP to be irrigated. Likewise, where the discharge section 24 has an inboard portion 25 and an outboard portion 26, different sizes of tubes 11 will be provided where the length $L_I$ of the inboard portion 25 will be different to accommodate different sizes of body parts BP. In each instance, it will be appreciated that each of the discharge openings 21 has a diameter smaller than the diameter of the fluid passage 16 through the perforated section 18 so as to prevent material from entering the fluid passage 16 through the discharge openings 21 which have a size sufficiently large to block the fluid passage 16.

Figure 5:
FIG. 5 is a view illustrating an installation needle for use with the invention.

The irrigation tube 11 may be installed in the body part BP during a surgical procedure or may be installed without resorting to a surgical procedure. When the irrigation tube 11 is to be installed without a surgical procedure, a solid needle 58 seen in FIG. 5 may be used. Such needles are conventionally available and are equipped with a threaded portion 59 on one end thereof designed to be screwed into the end of a piece of tubing to pull the tubing through the body part. The threaded portion 59 is selected so as to be screwed into the end 19 of the inlet section 22 of the tube 11. Preferably, the outside diameter of the needle 58 should be equal to or slightly less than the outside diameter of the inlet section 22 of the tube 11. The needle 58 can then be inserted through the body part and pulled to pull the tube 11 into place in the body part with the inlet section 22 passing therethrough followed by the perforated section 18. The tube 11 is pulled through the body part until the perforated section 18 is located in registration with that portion of the body part to be irrigated. This usually causes the transition portion 28 in the discharge section 24 to engage the surface of the body part to seal tube 11 thereto. It will be appreciated that the body part may be internally viewed through a fluoroscope as the needle 58 is inserted therethrough. Likewise, the tube 11 may be treated with an appropriate material so that the tube 11 may be seen with the fluoroscope as it is installed in the body part so that the perforated section 18 can be accurately located within the body part. After the tube 11 is installed in the body part BP, the needle 58 is removed and the fluid source 12 and vacuum source 14 are connected thereto to complete the system.

Various fluid sources 12 may be used in the invention. The particular fluid source 12 illustrated is an I.V. bottle 35 typically supported at an elevated position on an appropriate stand (not shown) so that its height above the patient can be adjusted. The bottle 35 is filled with the desired treatment solution to be used and its outlet tube 36 is connected to a conventional drop chamber 38. The outlet of drop chamber 38 is in turn connected to the end 19 of the inlet section 22 of irrigation tube 11 by a piece of tubing 39 equipped with a flow control valve 40 so that the treatment fluid flows by gravity into tube 11.

The rate of flow of the treatment fluid out of the bottle 35 is controlled by valve 40 and can be visually monitored in drop chamber 38. While valve 40 is illustrated as a manually adjustable valve, automatic flow regulating mechanisms as are known in the art may be substituted therefor. The treatment fluid thus flows down the fluid passage 16 in irrigation tube 11 toward the perforated section 18 at the rate established by the valve 40. It will also be appreciated that the treatment fluid is flowing into tube 11 continuously. While the flow rate may be varied as required, it has been found that flow rates of one drop/5 sec. to one drop/sec. are adequate for most applications.

Various vacuum sources 14 may be used with the invention. The particular vacuum source 14 illustrated is a vacuum pump 41 equipped with a controller 42 to control the operation of pump 41. The inlet to vacuum pump 41 is connected to the discharge of a vacuum receiver 44 while the inlet to the vacuum receiver 44 is connected to the end 20 of the discharge section 24 of the irrigation tube 11 by a piece of tubing 45. It will thus be seen that, when the vacuum pump 41 is operating, a vacuum will be imposed in the fluid passage 16 through the irrigation tube 11 via the vacuum receiver 44 and the tube 45. The controller 46 is constructed and arranged to intermittently operate the vacuum pump 41 so as to intermittently impose a vacuum in the fluid passage 16 in tube 11. The controller 42 may be adjustable so that the duration of the "on" cycle and the "off" cycle of the vacuum pump 41 may be adjustable. The time that the vacuum is not being imposed should be adjusted to permit adequate diffusion of the treatment fluid into the body part.

One vacuum pump which has been used satisfactorily has a built-in controller and is sold commercially by Gomco Surgical Manufacturing Corp. of Brooklyn, N.Y., as their Model 76A Thermontic Drainage Pump. This particular pump has a fixed cycle of 15–20 seconds "on" followed by 4–8 seconds "off" and can be used to supply vacuums of 120 mm mercy or 90 mm mercury. Typically, the higher vacuum is used.

When the vacuum pump 41 is not operating, the treatment fluid from the fluid source 12 will flow down the fluid passage 16 in the inlet section 22 of the irrigation tube 11 and will be discharged therefrom out through the openings 21 in the perforated section 18 of the tube 11 into the body part around the tube 11. This allows the treatment fluid to diffuse into the body part.

When the vacuum pump is operating, however, it will be seen that the vacuum imposed in the fluid passage 16 through tube 11 will draw treatment fluid along the passage 16 through the perforated section 18 and the discharge section 24 of the tube 11. Also, the vacuum is imposed through at least some of the discharge openings 21 in the perforated section 18 of the tube 11 on the fluids surrounding the perforated sections of the tube 11 in the body part BP. This causes the fluids in the body part BP to be withdrawn therefrom through the openings 21 into the fluid passage 16 and then withdrawn out through the discharge section 24 in the tube 11. The treatment fluid in the inlet section 22 withdrawn through the discharge section 24 without flowing out through the openings 21 keeps the fluid passage 16 in the perforated section 18 and discharge section 24 clear. The time that the vacuum is being imposed should be selected to prevent an excessive amount of the treatment fluid in inlet section 22 of tube 11 from being withdrawn during the "on" cycle.

As soon as the vacuum pump 41 ceases its operation, the vacuum is removed and the treatment fluid continues flowing down the inlet section 22 passing out into the body part BP through the openings 21. This alternating flow out through the discharge opening 21 into the body part BP and from the body part BP into the tube 11 through the openings 21 keeps the openings 21 cleared of any blockage due to any free floating material in the body part BP such as blood clots. This alternate discharge of the treatment fluid through the openings 21 into the body part and the subsequent withdrawal of the treatment fluid together with any fluids that become intermixed therewith in the body part BP serves to keep the body part BP flushed to reduce the likelihood of infection.

Although the intermittent operation of the vacuum source 14 is preferred, it will be appreciated that some of the treatment fluid will diffuse into the body part BP through openings 21 even though the vacuum source 14 is continuously operating. This is because some of the treatment fluid will pass out into the body part through those openings 21 nearer the inlet section 22 of tube 11 and then be withdrawn back into the tube 11 through the openings 21 nearer the discharge section 24.

The treatment fluid may be any of a variety of fluids such as a sterile saline solution or such a solution with any appropriate medication mixed therein. Thus, the irrigation system is to be used to keep the body part clean and/or treat the body part with appropriate medication to reduce any infection.

It will be appreciated that some means must be provided for maintaining back pressure in the perforated section 18 of the tube 11 while the vacuum pump 41 is not operating so as to force the treatment fluid flowing into the perforated section 18 through the inlet section 22 out through the discharge openings 21 into the body part BP. If such a retention means were not provided, the treatment fluid can simply flow along the fluid passage 16 into the discharge section 24 without flowing out through the openings 21. To provide this retention means, FIG. 1 shows a loop 50 formed in the discharge section 24 after it passes out of the body part BP. By using loop 50, the vacuum pump 41 is free to withdraw the fluid through the discharge section 24; however, the treatment fluid flowing from the fluid source 12 when the vacuum is not operating will fill the loop 50 up to a level sufficiently to cause the treatment fluid to be forced out of the discharge openings 21 into the body part BP. Typically, the uppermost portion of the loop 50 is at least as high as the uppermost discharge openings 21 through the perforated section 18 and preferably is located at a level about equal to that where the tube 11 enters the body part BP. The loop 50 should be located as close as practical to the point where tube 11 exits the body part to minimize the vaolume of fluid required to force the treatment fluid out through opening 21.

Figure 2:
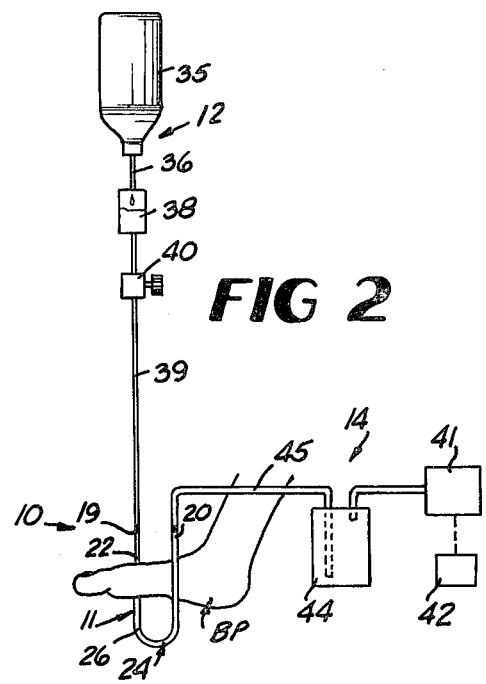
FIG. 2 is a view similar to FIG. 1 illustrating a different arrangement of the invention.
Figure 3:
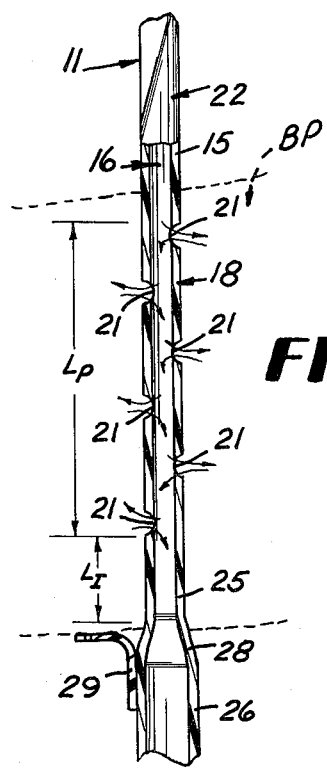
FIG. 3 is an enlarged longitudinal cross-sectional view of a portion of the irrigation tube of the invention.

FIG. 2 shows an alternate method of providing a back pressure to force the treatment fluid out through the discharge openings 21 in the tube 11 when the vacuum pump 41 is not operating. This procedure provides locating at least the vacuum receiver 44 above the level of the body part BP so that the discharge section 24 of the tube 11 extends upwardly above the level of the perforated section 18 in the tube 11. Thus, the treatment fluid from the source 12 will flow along the discharge section 24 of the tube 11 until the treatment fluid is forced out of the discharge openings 21 of the perforated section 18.

In both of these instances, it will be seen that the tube 11 is located in the body part BP so that the inlet section 22 passes into the body part BP through the top of the body part BP while the discharge section 24 exits the body part BP through its bottom. It will be appreciated that the direction in which the tube 11 extends through the body part BP may be used to provide the back pressure necessary to force the treatment fluid out of the openings 21 through the perforated section 18 when the vacuum pump 41 is not operating.

Figure 4:
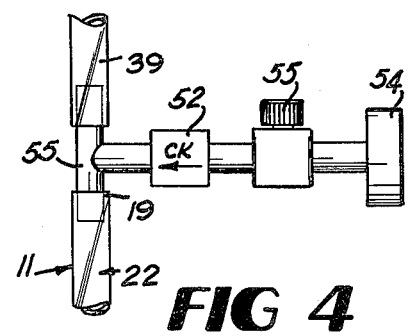
FIG. 4 is an enlarged view showing a venting means for the invention.

It has further been found that it is sometimes difficult to impose a sufficient vacuum in the fluid passage 16 through the tube 11 to insure that the fluid will be withdrawn from the body part BP together with a sufficient amount of the treatment fluid entering the tube 11 to keep the tube 11 clean. This is especially true where the size of the fluid passage 16 through the tube 11 is very small. To assist in the withdrawal operation, a venting means 51 may be provided between the body part BP and the fluid source 11 as illustrated in FIG. 4, so that, when a vacuum is imposed in a fluid passage through the tube 11, air can be drawn into the fluid passage 16 and passed therethrough along with any fluid in passage 16 while the vacuum pump 41 is operated. The venting means 51 includes a check valve 52 operating so as to only allow air to enter the passage 16 through the tube 11. The check valve 52 may be provided with an appropriate filter 54 to keep the air passing into the fluid passage 16 clean. To regulate the amount of air passing into tube 11, a regulating valve 55 may be provided. While the venting means 51 may be connected to the system ast any position between the body part BP and the fluid source 12, it is preferable that the venting means 51 may be located as close as possible to the body part BP. One convenient location is to locate the venting means 51 on the connector 55 connecting the end of the inlet section 22 to the tubing from the fluid source 12. Likewise, it will be appreciated that additional fluid may be injected into the tube 11 through the venting means 51 under sufficient pressure to clear any unusual blockage that may occur in the fluid passage 16 and/or discharge openings 21 in the tube 11.

What is claimed as invention is:

1. A method of irrigating a wound in a body part with a treatment liquid comprising the steps of:
    placing a piece of tubing having a perforated section therein in the body part so that the perforated section is generally straight and located in the vicinity of the wound in the body part to be irrigated and opposite ends of the tubing extend exteriorly of the body part;
    connecting one end of the tubing to a source of the treatment liquid;
    connecting the opposite end of the piece of tubing to a vacuum pump;
    operating the source of treatment liquid so that the treatment liquid continuously passes along the tubing toward the perforated section so that some of the treatment liquid passes into the wound through the perforated section; and
    operating the vacuum pump to impose a vacuum in the tubing and withdraw liquid from the wound through the perforated section while at the same time withdrawing treatment fluid past the perforated section without passing into the wound to keep the passage through the tubing from becoming blocked.

2. The method of claim 1 further including the step of intermittently operating the vacuum pump.

3. The method of claim 2 further including the step of creating a back pressure in the treatment liquid flowing past the perforated section in the tubing toward the opposite end thereof while the vacuum is not being imposed so as to force the treatment liquid to flow out of the tubing through the perforated section into the body part while still leaving the perforated section in communication with said vacuum pump so that, when the vacuum is imposed, the back pressure is overcome to withdraw liquid from the wound as well as treatment fluid past the perforated section.

4. The method of claim 3 further including the step of venting the tubing between the body part and the source of treatment liquid so as to permit air to be drawn into the tubing while the vacuum is being imposed while preventing fluid from passing out of the tubing where the tubing is vented.

5. The method of claim 4 wherein the step of intermittently operating the vacuum pump includes alternatively imposing the vacuum for a first prescribed period of time and not imposing the vacuum for a second prescribed period of time.

6. The method of claim 5 wherein said first prescribed period of time is 15–20 seconds and said second prescribed period of time is 4–8 seconds.

* * * * *